US009427391B2

(12) United States Patent
Peffly et al.

(10) Patent No.: US 9,427,391 B2
(45) Date of Patent: Aug. 30, 2016

(54) PERSONAL CARE COMPOSITIONS CONTAINING CATIONIC SYNTHETIC COPOLYMER AND A DETERSIVE SURFACTANT

(75) Inventors: Marjorie Mossman Peffly, Cincinnati, OH (US); Mark Anthony Brown, Union, KY (US); James Anthony Staudigel, Loveland, OH (US); Jun Ji Zhang, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1618 days.

(21) Appl. No.: 11/650,921

(22) Filed: Jan. 8, 2007

(65) Prior Publication Data

US 2007/0207109 A1 Sep. 6, 2007

Related U.S. Application Data

(60) Provisional application No. 60/774,533, filed on Feb. 17, 2006, provisional application No. 60/757,343, filed on Jan. 9, 2006.

(51) Int. Cl.
*A61K 8/81* (2006.01)
*A61K 8/46* (2006.01)
*A61Q 5/02* (2006.01)
*A61Q 5/12* (2006.01)

(52) U.S. Cl.
CPC ............. *A61K 8/8158* (2013.01); *A61K 8/463* (2013.01); *A61Q 5/02* (2013.01); *A61Q 5/12* (2013.01); *A61K 2800/5426* (2013.01)

(58) Field of Classification Search
None
See application file for complete search history.

(56) References Cited

U.S. PATENT DOCUMENTS

| | | |
|---|---|---|
| 1,110,756 A | 9/1914 | Duryea |
| 2,438,091 A | 3/1948 | Lynch |
| 2,528,378 A | 10/1950 | Mannheimer |
| 2,658,072 A | 11/1953 | Kosmin |
| 2,694,668 A | 11/1954 | Fricke |
| 2,809,971 A | 10/1957 | Bernstein et al. |
| 2,826,551 A | 3/1958 | Geen |
| 3,152,046 A | 10/1964 | Kapral |
| 3,236,733 A | 2/1966 | Karsten et al. |
| 3,332,880 A | 7/1967 | Kessler et al. |
| 3,753,196 A | 8/1973 | Kurtz et al. |
| 3,761,418 A | 9/1973 | Parran, Jr. |
| 3,929,678 A | 12/1975 | Laughlin et al. |
| 3,964,500 A | 6/1976 | Drakoff |
| 3,986,890 A | 10/1976 | Richter et al. |
| 4,052,226 A | 10/1977 | Verbanac |
| 4,089,945 A | 5/1978 | Brinkman et al. |
| 4,298,494 A | 11/1981 | Parslow et al. |
| 4,323,683 A | 4/1982 | Bolich, Jr. et al. |
| 4,345,080 A | 8/1982 | Bolich, Jr. |
| 4,364,837 A | 12/1982 | Pader |
| 4,379,753 A | 4/1983 | Bolich, Jr. |
| 4,387,017 A | 6/1983 | McEntire et al. |
| 4,470,982 A | 9/1984 | Winkler |
| 4,767,463 A | 8/1988 | Brode et al. |
| 4,885,107 A | 12/1989 | Wetzel |
| 4,890,314 A | 12/1989 | Judd et al. |
| 4,977,252 A | 12/1990 | Chiu |
| 5,104,646 A | 4/1992 | Bolich, Jr. et al. |
| 5,106,609 A | 4/1992 | Bolich, Jr. et al. |
| 5,185,176 A | 2/1993 | Chiu |
| 5,186,928 A | 2/1993 | Birtwistle |
| RE34,584 E | 4/1994 | Grote et al. |
| 5,500,152 A | 3/1996 | Helliwell |
| 5,635,171 A | 6/1997 | Nadaud |
| 5,733,854 A | 3/1998 | Chowdhary et al. |
| 5,795,397 A | 8/1998 | Shi et al. |
| 5,977,036 A | 11/1999 | Guskey |
| 6,096,524 A | 8/2000 | Shi et al. |
| 6,153,569 A | 11/2000 | Halloran |
| 6,228,377 B1 | 5/2001 | Sebillotte-Arnaud |
| 6,290,944 B1 | 9/2001 | Garnier et al. |
| 6,365,140 B1 | 4/2002 | Melby et al. |
| 6,380,379 B1 | 4/2002 | Antrim et al. |
| 6,383,993 B1 | 5/2002 | Maurin et al. |
| 6,387,855 B1 | 5/2002 | De La Mettrie |
| 6,727,220 B1 | 4/2004 | Grainger et al. |
| 6,930,078 B2 | 8/2005 | Wells et al. |
| 7,157,413 B2 | 1/2007 | Lazzeri et al. |
| 7,244,697 B2 | 7/2007 | Terada |
| 7,283,243 B2 | 10/2007 | Langford et al. |
| 7,439,214 B2 | 10/2008 | Utz et al. |
| 2001/0051143 A1 | 12/2001 | Cottrell |
| 2002/0012646 A1 | 1/2002 | Royce et al. |
| 2003/0045708 A1 | 3/2003 | Magallanes et al. |

(Continued)

FOREIGN PATENT DOCUMENTS

| | | |
|---|---|---|
| DE | 4129986 | 9/1991 |
| DE | 69302141 | 10/1996 |

(Continued)

OTHER PUBLICATIONS

Encyclopedia of Polymer Science and Engineering, vol. 15, 2d ed., pp. 204-308, John Wiley & Sons, Inc. (1989).
Laughlin, R.G. (1994), "The Aqueous Phase Behavior of Surfactants," 182, 8.2.
US-1991/000784278, Oct. 29, 1991, Wells, et al.
Crepaldi, E.L. et al., *J. Colloid Interfac. Sci.* 2002, 248, 429-42.
Morioka, et al., *Inorg. Chem.* 1999, 38, 4211-6.

*Primary Examiner* — David J Blanchard
*Assistant Examiner* — Garen Gotfredson
(74) *Attorney, Agent, or Firm* — Carl J. Roof

(57) ABSTRACT

The present invention relates to a personal care composition with a synthetic random copolymer having a net positive charge, a detersive surfactant; and an aqueous carrier.

20 Claims, No Drawings

(56) References Cited

U.S. PATENT DOCUMENTS

| | | |
|---|---|---|
| 2003/0108507 A1 | 6/2003 | Clipson et al. |
| 2003/0130145 A1 | 7/2003 | Patel et al. |
| 2003/0134759 A1 | 7/2003 | Geary et al. |
| 2003/0154883 A1 | 8/2003 | MacKey et al. |
| 2003/0223951 A1 | 12/2003 | Geary et al. |
| 2004/0010074 A1 | 1/2004 | Cadena et al. |
| 2004/0010106 A1* | 1/2004 | Liu .................. 526/303.1 |
| 2004/0037794 A1 | 2/2004 | Dubief |
| 2004/0077510 A1 | 4/2004 | Lazzeri et al. |
| 2004/0105833 A1 | 6/2004 | Fack et al. |
| 2004/0146475 A1* | 7/2004 | Peffly et al. ........... 424/70.13 |
| 2004/0213751 A1 | 10/2004 | Schwartz et al. |
| 2004/0234483 A1 | 11/2004 | Peffly et al. |
| 2004/0234484 A1 | 11/2004 | Peffly et al. |
| 2005/0069511 A1 | 3/2005 | Magnet et al. |
| 2005/0101499 A9 | 5/2005 | Lazzeri et al. |
| 2006/0002880 A1 | 1/2006 | Peffly et al. |
| 2006/0052273 A1 | 3/2006 | Terada |
| 2006/0099167 A1 | 5/2006 | Staudigel |
| 2007/0160555 A1 | 7/2007 | Staudigel |
| 2007/0207109 A1 | 9/2007 | Peffly et al. |
| 2008/0139432 A1 | 6/2008 | Peffly et al. |
| 2008/0206179 A1 | 8/2008 | Peffly et al. |
| 2008/0206355 A1 | 8/2008 | Schwartz et al. |
| 2009/0087398 A1 | 4/2009 | Brown et al. |
| 2009/0176674 A1 | 7/2009 | Peffly et al. |

FOREIGN PATENT DOCUMENTS

| | | |
|---|---|---|
| DE | 19921707 | 11/2000 |
| DE | 10128799 | 1/2003 |
| DE | 10216506 | 10/2003 |
| EP | 156646 A1 | 10/1985 |
| EP | 0610407 A1 | 8/1994 |
| EP | 0659472 A3 | 8/1995 |
| EP | 0577519 B1 | 4/1996 |
| EP | 0742007 A1 | 11/1996 |
| EP | 1047373 B1 | 10/1999 |
| EP | 1051967 | 11/2000 |
| EP | 0869766 B1 | 11/2001 |
| FR | 2693104 | 1/1994 |
| FR | 2767718 | 3/1999 |
| FR | 2785800 | 5/2000 |
| GB | 849433 | 9/1960 |
| JP | 55043138 | 3/1980 |
| JP | 2007017826 | 1/1995 |
| JP | 2001010934 | 6/1999 |
| JP | 2000103724 A2 | 4/2000 |
| JP | 2003-277243 A | 10/2003 |
| WO | WO-9308787 A2 | 5/1993 |
| WO | WO-9818434 A1 | 5/1998 |
| WO | WO-0028949 A1 | 10/1999 |
| WO | WO-0197761 A1 | 6/2000 |
| WO | WO-02078654 | 10/2002 |
| WO | WO-03084486 | 10/2003 |

* cited by examiner

PERSONAL CARE COMPOSITIONS CONTAINING CATIONIC SYNTHETIC COPOLYMER AND A DETERSIVE SURFACTANT

CROSS REFERENCE TO RELATED APPLICATION(S)

This application claims the benefit of U.S. Provisional Application No. 60/774,533, filed Feb. 17, 2006; and U.S. Provisional Application No. 60/757,343, filed Jan. 9, 2006.

FIELD OF THE INVENTION

The present invention relates to personal care compositions with improved lather and conditioning performance which comprise select synthetic copolymers.

BACKGROUND OF THE INVENTION

Conditioning personal care compositions comprising various combinations of detersive surfactant and hair conditioning agents are known. These personal care compositions typically comprise an anionic detersive surfactant in combination with a conditioning agent such as silicone, hydrocarbon oil, fatty esters, or combinations thereof. These personal care compositions have become more popular among consumers as a means of conveniently obtaining hair conditioning and hair cleansing performance all from a single hair care product.

Many conditioning personal care compositions, however, do not provide sufficient deposition of conditioning agents onto hair or skin during the application process; if deposition is possible, it is only possible in formulations with relatively low levels of anionic surfactant. Without such deposition, large proportions of conditioning agent are rinsed away during the application process and therefore provide little or no conditioning benefit. Without sufficient deposition of the conditioning agent on the hair or skin, relatively high levels of conditioning agents may be needed in the personal care composition to provide adequate hair or skin conditioning performance. Such high levels of a conditioning agent, however, can increase raw material costs, reduce lathering, and present product stability concerns. Additionally, limitations on total anionic surfactant in order to form coacervate can limit the lather potential for a formula, or result in the need for higher levels of more expensive amphoteric surfactants to achieve good lather.

One known method for improving deposition of a hair conditioning agent onto hair involves the use of certain cationic deposition polymers. These polymers may be synthetic, but are most commonly natural cellulosic or guar polymers that have been modified with cationic substituents.

The formation of coacervate upon dilution of the personal care composition with water is important to improving deposition of various conditioning actives, especially those that have small droplet sizes (i.e., ≤2 microns). Dilution generally occurs during the usage of the personal care composition, for example, when a person applies a personal care composition to wet hair, the product is automatically diluted with water. In order to form coacervate, a personal care composition containing typical cationic polymers, such as natural cellulosic or guar polymers that have been modified with cationic substituents, tend to be significantly limited in total anion concentrations in order to achieve adequate levels of coacervate upon dilution. For example, limiting the total level of sulfate in a sulfated anionic surfactant will encourage coacervate formation but will limit the volume of lather that can be achieved with a particular personal care cleansing composition. Thus, for low cost, high lathering, coacervate forming compositions, it is desirable to use a cationic polymer that can form coacervate with higher levels of anionic surfactants.

A need still exists for improved conditioning and lather performance in personal care compositions.

It has now been found that select synthetic cationic polymers provide improved conditioning performance, especially wet hair conditioning, and improved deposition of dispersed hair conditioning agents onto hair or skin. These select polymers are especially effective at improving deposition of dispersed hair conditioning agents onto hair and skin, through coacervate formation upon dilution. In one embodiment, coacervate formation is optimized when formulated in combination with certain levels of anionic detersive surfactant in a personal care composition.

SUMMARY OF THE INVENTION

The present invention meets the aforementioned need by providing a personal care composition comprising:
  a) a synthetic random copolymer having a net positive charge comprising, based on the total number of monomeric units of the copolymer;
    i.) a nonionic monomer unit of the following formula:

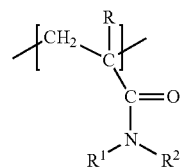

where R is H or $C_{1-4}$ alkyl; and $R^1$ and $R^2$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and
    ii.) a cationic monomer unit with 2 or more positive charges of the following formula:

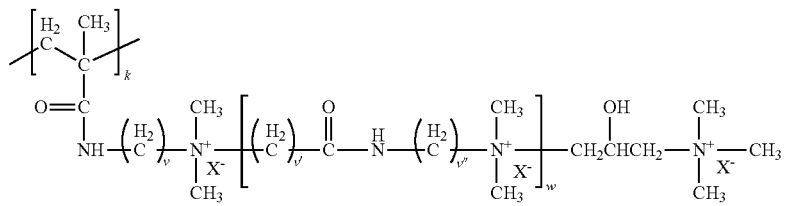

where k=1, each of v, v', and v" is independently an integer of from 1 to 6, w is zero or an integer of from 1 to 10, and $X^-$ is an anion.

and;

b) a detersive surfactant; and c) an aqueous carrier.

One embodiment comprises an anionic surfactant system having an optimized ethoxylate level and anion level.

These and other features, aspects, and advantages of the present invention will become evident to those skilled in the art from a reading of the present disclosure.

DETAILED DESCRIPTION OF THE INVENTION

While the specification concludes with claims that particularly point out and distinctly claim the invention, it is believed the present invention will be better understood from the following description.

The personal care compositions of the present invention comprise a synthetic random copolymer, a detersive surfactant, and an aqueous carrier. Each of these essential components, as well as preferred or optional components, is described in detail hereinafter.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

The term "charge density" as used herein, means the ratio of the number of positive charges on a monomeric unit of which a polymer is comprised to the molecular weight of said monomeric unit. The charge density multiplied by the polymer molecular weight determines the number of positively charged sites on a given polymer chain.

The term "coacervate" as used herein, means the complex which forms between surfactant and polymer that may either be soluble or insoluble in the neat personal care composition, and which may become less soluble upon dilution and thus yielding an increase in its level of phase separation or precipitate in solution.

The term "comprising" means that unrecited steps, elements or other ingredients are not necessarily excluded. This term encompasses the terms "consisting of" and "consisting essentially of." The compositions and methods/processes can comprise, consist of, and consist essentially of the essential elements and limitations of the invention described herein, as well as any of the additional or optional ingredients, components, steps, or limitations described herein.

The term "floc" as used herein, means localized clusters of agglomerated, insoluble coacervate. Any floc size disclosed herein is obtained using the HORIBA® LA-910 Laser Diffraction Particle Size Analyzer and is reported as a volume average floc diameter.

The term "isotropic" as used herein, means a particular phase structure of coacervate wherein the structure is "identical along any three orthogonal directions in space, and is therefore dark or 'nonbirefringent' when viewed between crossed polarized light. (One direction is 'orthogonal' to another if the vector component of the first, in the direction of the second, is zero.) (Laughlin, R. G. (1994). "The Aqueous Phase Behavior of Surfactants," 182, 8.2).

The term "linear charge density" as used herein, means the ratio of the number of positive charges on a monomeric unit of which the polymer is comprised to the length in Angstroms of said monomeric unit. The length of the monomeric unit is calculated by multiplying the ratio of the nonionic monomer by the length, in Angstroms, of the nonionic monomer plus the ratio of cationic monomer multiplied by the length, in Angstroms, of the cationic monomer.

The term "mass charge density" as used herein, means the ratio of the number of positive charges on a monomeric unit of which a polymer is comprised to the molecular weight of said monomeric unit. A molecular weight of the monomeric unit is calculated by multiplying the ratio of the nonionic monomer by the molecular weight of the nonionic monomer plus the product of the ratio of cationic monomer multiplied by the molecular weight of the cationic monomer.

The term "neat" as used herein, means the unadulterated form of the personal care composition (i.e., the altering of the present composition through dilution with water).

The term "polymer" as used herein shall comprise materials whether made by polymerization of one type of monomer or made by two (i.e., copolymers) or more (i.e., terpolymers) types of monomers.

The term "water insoluble" as used herein, means that the polymer is not soluble in water in the personal care composition. Thus, the polymer is not miscible with water. In general, solubility is determined at about 25° C.

The term "water soluble" as used herein, means that the polymer is soluble in water in the personal care composition. In general, the polymer should be soluble at about 25° C. at a concentration of at least about 0.1% by weight of the water solvent, preferably at least about 1%, more preferably at least about 5%, most preferably at least about 15%.

One embodiment is directed to the surprising discovery that compositions combining certain specific levels and ratios of surfactant as described by the overall anion and ethoxylate values maximize the conditioning benefit via maximization of coacervate formation. Moreover, while the optimum surfactant blend is different for each polymer, it has been discovered that the optimum surfactant composition can be described by two parameters. These parameters include anion and ethoxylate values that, when expressed as a function of the polymer's charge density and molecular weight, maximize the formation of coacervate.

Coacervates, without being limited to a particular theory, provide improved hair and skin conditioning without any additional conditioning actives. Further, when dispersed conditioning agent droplets are added to the matrix, the coacervate provides an improved mechanism for conditioning agent deposition, yielding conditioning agent deposition that results in even more of a conditioning benefit.

Synthetic Copolymer

The personal care compositions comprise synthetic copolymers that, in combination with the detersive surfactant component, an aqueous carrier and other optional components herein, form coacervate upon dilution. The polymers are formulated in a personal care composition that provides improved conditioning performance when formulated, even without additional conditioning actives, and also provides improved deposition of the conditioning agent onto the hair or skin. The monomer units of the synthetic copolymer may be arranged to form random copolymers and grafted copolymers. Random copolymers are preferred.

The concentration of the synthetic copolymer in the shampoo composition ranges about 0.01% to about 5%, preferably from about 0.05% to about 3%, more preferably from about 0.075% to about 1%, by weight of the composition.

Another embodiment comprises personal care compositions comprising a synthetic copolymer of sufficiently high molecular weight to effectively enhance the deposition of the conditioning active components of the personal care composition described herein. The average molecular weight of the synthetic copolymers is generally between about 10,000 and about 10 million, preferably between about 100,000 and about 3 million, still more preferably between about 200,000 and about 2 million.

In a further embodiment, the synthetic copolymers have mass charge densities of from about 0.1 meq/gm to about 6.0 meq/gm and more preferably from about 0.5 meq/gm to about 3.0 meq/gm, at the pH of intended use of the personal care composition. The pH will generally range from about pH 3 to about pH 9, and more preferably between about pH 4 and about pH 8.

In yet another embodiment, the synthetic copolymers have linear charge densities from at least about 2 meq/A to about 500 meq/A, and more preferably from about 20 meq/A to about 200 meq/A, and most preferably from about 25 meq/A to about 100 meq/A.

Nonionic Monomer Unit

The synthetic copolymers comprise the nonionic monomer unit represented by the following Formula I:

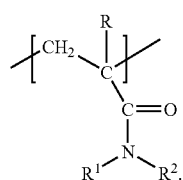

I where R is H or $C_{1-4}$ alkyl; and $R^1$ and $R^2$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl.

In one embodiment, nonionic monomer unit is acrylamide (AM), i.e., where R, $R^1$, and $R^2$ are all H as shown below:

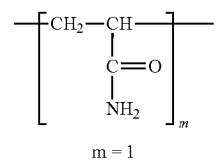

m = 1

Another preferred nonionic monomer unit is methacrylamide (MethAM), i.e., where R is $C_1$ alkyl, and $R^1$ and $R^2$ are each H respectively:

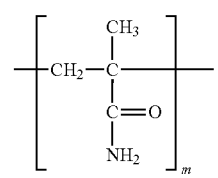

m = 1

However, the other acrylamide derivatives within the scope of the formula set out above are also contemplated to be part of the present invention where polyacrylamide and copolymers using acrylamide monomers are useful.

The nonionic monomer portion of the synthetic copolymers is present in an amount from about 50% to about 99.5% by weight of the total copolymer. Preferably, this amount is from about 70% to about 99%, still more preferably from about 80% to about 99% by weight of the synthetic copolymer.

Cationic Monomer Unit

The synthetic copolymers also comprise the cationic monomer unit represented by Formula II:

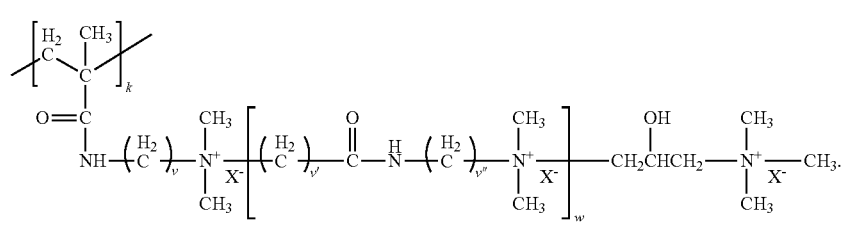

II where k=1, each of v, v', and v" is independently an integer of from 1 to 6, w is zero or an integer of from 1 to 10, and X⁻ is an anion.

In one embodiment, a structure is present where k=1, v=3 and w=0, z=1 and X⁻ is Cl⁻ according to Formula II, above, to form the following structure:

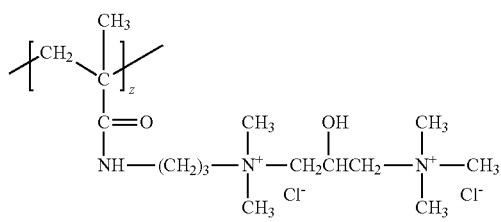

The above structure may be referred to as diquat.

Yet another embodiment is achieved by the structure formed wherein v and v" are each 3, v'=1, w=1, y=1 and X⁻ is Cl⁻ according to Formula II, such as:

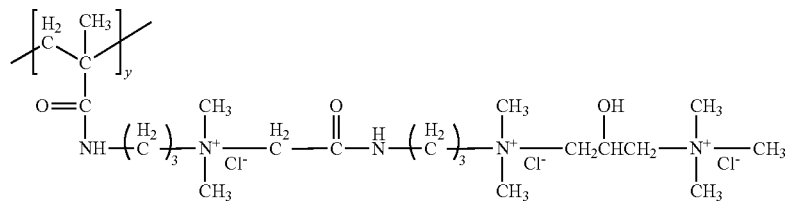

The above structure may be referred to as triquat.

Suitable cationic monomers can be made by, for example, the methods described in U.S. Patent Application Publication No. 2004/0010106 A1.

In one embodiment, the cationic monomer portion of the synthetic copolymers is present in an amount from about 0.5% to about 50% by weight of the total copolymer. Preferably, this amount is from about 1% to about 30% and most preferably from about 1% to about 20% by weight of the synthetic copolymer.

Method of Making the Triquat Monomer

Non limiting examples of polymerization techniques are described in U.S. Pat. No. 4,387,017, European Patent No. EP 156,646 and U.S. Patent Publication No. 2004/0010106 A1.

In one embodiment, the triquat monomer is formed by executing a three-step reaction in a jacketed reactor flask equipped with mechanical stirrer, gas inlet, condenser, and thermometer. The mechanical stirring and air purging is maintained throughout the reactions. First, 340.52 g of dimethylaminopropyl methacrylamide (DMAPMA), 238.75 g of methyl chloroacetate, 0.34 g of 4-methoxyphenol (MEHQ) and 425 g of methanol are added to the reactor and heated at about 65-70° C. for approximately 5 hours to yield (methacrylamidopropyl)(methoxy-carbonylmethyl)dimethylammonium chloride (MMDMAC). Samples are taken every 2 hours and analyzed by HPLC analysis and Cl titrated with AgNO₃ to ensure 100% conversion. Second, 0.365 g of MEHQ, and 224.5 g of dimethylaminopropylamine (DMAPA) is slowly added to MMDMAC solution after it is cooled to room temperature (about 25° C.). An exothermic reaction is observed, and the mixture appears light yellow in color. Heat is continued at about 65-70° C. for about 2 hours, then methanol is distilled out under vacuum. After confirming that all ester is converted into amide by HPLC in the second step, 637 g of 65% (3-chloro-2-hydroxypropyl) trimethylammonium chloride (Quat-188) is added. Third, the temperature is maintained at about 65-70° C. for about 2 hours. The reaction is continued in water for another hour to yield the triquat monomer. The triquat so synthesized is expected to contain a small amount of multiple quats as an impurity due to the slight excess use of chloroacetate and DMAPA. The multiple quats are not a concern for polymerization and for the uses of the triquat. If a highly pure triquat or multiple quats is required, the excess amount of chloroacetate and DMAPA can be removed under vacuum.

Detersive Surfactant

The personal care compositions comprise a detersive surfactant system. The detersive surfactant system is included to provide cleaning performance to the composition. The detersive surfactant system comprises at least one anionic surfactant, and optionally an amphoteric surfactant, a zwitterionic surfactant, a cationic surfactant, a nonionic surfactant, or a combination thereof. Such surfactants should be physically and chemically compatible with the essential components described herein, or should not otherwise unduly impair product stability, aesthetics, or performance.

Suitable anionic surfactant components for use in the personal care composition herein include those that are known for use in hair care or other personal care compositions. The concentration of the anionic surfactant system in the personal care composition should be sufficient to provide the desired cleaning and lather performance, and generally ranges from about 5% to about 50%, preferably from about 8% to about 30%, more preferably from about 10% to about 25%, by weight, of the composition.

In considering the performance characteristics of a personal care composition, such as coacervate formation, wet conditioning performance, dry conditioning performance, and conditioning agent deposition on hair, it is desirable to optimize the levels and types of surfactants in order to maximize the performance potential of polymer systems. In one embodiment, the anionic surfactant system for use in the personal care compositions have an ethoxylate level and an anion level, wherein the ethoxylate level is from about 1 to about 10, and wherein the anion level is from about 1 to about 10. The combination of such an anionic surfactant system with the synthetic copolymer provides enhanced deposition of conditioning agents to hair and/or skin without reducing cleansing or lathering performance.

An optimal ethoxylate level is calculated based on the stoichiometry of the surfactant structure, which in turn is based on a particular molecular weight of the surfactant where the number of moles of ethoxylation is known. Likewise, given a specific molecular weight of a surfactant and an anionization reaction completion measurement, the anion level can be calculated. Analytical techniques have been developed to measure ethoxylation or anionization within surfactant systems. The Level of Ethoxylate and the Level of Anion representative of a particular surfactant system are calculated from the percent ethoxylation and percent anion of individual surfactants in the following manner:

Level of Ethoxylate in a composition=percent ethoxylation multiplied by percent active ethoxylated surfactant (based upon the total weight of the composition).

Level of Anion in a composition=percent anion in ethoxylated surfactant multiplied by percent active ethoxylated surfactant (based upon the total weight of the composition) plus percent anion in non-ethoxylated surfactant multiplied by percent active non-ethoxylated surfactant (based upon the total weight of the composition).

If a composition comprises two or more surfactants having different respective anions (e.g., surfactant A has a sulfate group and surfactant B has a sulfonate group), the Level of Anion in the composition is the sum of the molar levels of each respective anion as calculated above.

Sample Calculation:

Example I shows an ethoxylated surfactant that contains 0.294321% ethoxylate and 0.188307% sulfate as the anion and a non-ethoxylated surfactant that contains 0.266845% sulfate as an anion.

Level of Ethoxylate in Example I=0.294321 multiplied by 6 (% active ethoxylated surfactant). Thus, the Level of Ethoxylate in the composition of Example I is approximately 1.77.

Level of Anion in Example I=0.188307 multiplied by 6 (% active ethoxylated surfactant) plus 0.266845 multiplied by 10 (% active non-ethoxylated surfactant). Thus, the Level of Anion in the composition of Example I is approximately 3.80.

In one embodiment, the detersive surfactant system comprises at least one anionic surfactant comprising an anion selected from the group consisting of sulfates, sulfonates, sulfosuccinates, isethionates, carboxylates, phosphates, and phosphonates. Preferably, the anion is a sulfate.

Preferred anionic surfactants suitable for use in the personal care compositions are alkyl sulfates and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from about 1 to about 10, and M is a cation such as ammonium, an alkanolamine such as triethanolamine, a monovalent metal cation such as sodium and potassium, or a polyvalent metal cation such as magnesium and calcium. Solubility of the surfactant will depend upon the particular anionic surfactants and cations chosen.

Preferably, R has from about 8 to about 18 carbon atoms, more preferably from about 10 to about 16 carbon atoms, even more preferably from about 12 to about 14 carbon atoms, in both the alkyl sulfates and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with from about 0 to about 10, preferably from about 2 to about 5, more preferably about 3, molar proportions of ethylene oxide, and the resulting mixture of molecular species having, for example, an average of 3 moles of ethylene oxide per mole of alcohol is sulfated and neutralized.

Specific non-limiting examples of alkyl ether sulfates which may be used in the personal care compositions comprise sodium and ammonium salts of coconut alkyl triethylene glycol ether sulfate, tallow alkyl triethylene glycol ether sulfate, and tallow alkyl hexa-oxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide. Such a mixture also comprises from about 0% to about 20% by weight. $C_{12-13}$ compounds; from about 60% to about 100% by weight of $C_{14-15-16}$ compounds; from about 0% to about 20% by weight of $C_{17-18-19}$ compounds; from about 3% to about 30% by weight of compounds having a degree of ethoxylation of 0; from about 45% to about 90% by weight of compounds having a degree of ethoxylation from about 1 to about 4; from about 10% to about 25% by weight of compounds having a degree of ethoxylation from about 4 to about 8; and from about 0.1% to about 15% by weight of compounds having a degree of ethoxylation greater than about 8.

Examples of anionic surfactants for use in the personal care compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and combinations thereof.

In addition to the sulfates, isethionates, sulfonates, sulfosuccinates described above, other potential anions for the anionic surfactant include phosphonates, phosphates, and carboxylates.

The personal care compositions may also comprise one or more additional surfactants selected from the group consisting of amphoteric surfactants, zwitterionic surfactants, cationic surfactants, and nonionic surfactants. Suitable amphoteric, zwitterionic, cationic, or nonionic surfactants for use in the personal care compositions herein include those which are known for use in hair care or other personal care compositions. The concentration of such surfactants preferably ranges from about 0.5% to about 20%, preferably from about 1% to about 10%, by weight of the composition. Non-limiting examples of suitable surfactants are described in U.S. Pat. Nos. 5,104,646 and 5,106,609, both to Bolich, Jr. et al.

Additional Surfactants

Zwitterionic or Amphoteric Surfactant

Suitable amphoteric or zwitterionic surfactants for use in the personal care composition herein include those which are known for use in hair care or other personal care compositions.

Amphoteric surfactants suitable for use in the personal care composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric surfactants for use in the personal care compositions comprise cocoamphoacetate, cocoamphodiacetate, lauroamphoacetate, lauroamphodiacetate, lauramine oxide, and mixtures thereof.

Zwitterionic surfactants suitable for use in the personal care composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines (i.e., cocoamidopropyl betaine, coco betaine), are preferred.

The personal care compositions may further comprise additional surfactants for use in combination with the surfactant component described hereinbefore. Other suitable anionic surfactants are the water-soluble salts of organic, sulfuric acid reaction products conforming to the formula $[R^1—SO_3-M]$ where $R^1$ is a straight or branched chain, saturated, aliphatic hydrocarbon radical having from about 8 to about 24, preferably from about 10 to about 18 carbon atoms; and M is a cation described hereinbefore. Non limiting examples of such surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil.

Other anionic surfactants suitable for use in the personal care compositions are the succinates, examples of which include disodium N-octadecylsulfosuccinate; disodium lauryl sulfosuccinate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfonates which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the personal care compositions are the beta-alkyloxy alkane sulfonates. These surfactants conform to the Formula II:

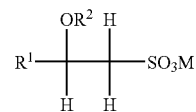

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore. Preferred anionic surfactants for use in the personal care compositions include sodium tridecyl benzene sulfonate, sodium dodecyl benzene sulfonate.

Amides, including alkanol amides, are the condensation products of fatty acids with primary and secondary amines or alkanolamines to yield products of the general Formula III:

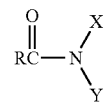

wherein RCO is a fatty acid radical and R is $C_{8-20}$; X is an alkyl, aromatic or alkanol (CHR'CH$_2$OH wherein R' is H or $C_{1-6}$ alkyl); Y is H, alkyl, alkanol or X. Suitable amides include, but are not limited to cocamide, lauramide, oleamide and stearamide. Suitable alkanolamides include, but are not limited to, cocamide DEA, cocamide MEA, cocamide MIPA, isostearamide DEA, isostearamide MEA, isostearamide MIPA, lanolinamide DEA, lauramide DEA, lauramide MEA, lauramide MIPA, linoleamide DEA, linoleamide MEA, linoleamide MIPA, myristamide DEA, myristamide MEA, myristamide MIPA, Oleamide DEA, Oleamide MEA, Oleamide MIPA, palmamide DEA, palmamide MEA, palmamide MIPA, palmitamide DEA, palmitamide MEA, palm kernelamide DEA, palm kernelamide MEA, palm kernelamide MIPA, peanutamide MEA, peanutamide MIPA, soyamide DEA, stearamide DEA, stearamide MEA, stearamide MIPA, tallamide DEA, tallowamide DEA, tallowamide MEA, undecylenamide DEA, undecylenamide MEA, PPG-2 Hydroxyethyl cocoamide, and PPG-2-Hydroxyethyl Coco/Isostearamide. The condensation reaction may be carried out with free fatty acids or with all types of esters of the fatty acids, such as fats and oils, and particularly methyl esters. The reaction conditions and the raw material sources determine the blend of materials in the end product and the nature of any impurities.

Suitable optional surfactants include nonionic surfactants. Any such surfactant known in the art for use in hair or personal care products may be used, provided that the optional additional surfactant is also chemically and physically compatible with the essential components of the personal care composition, or does not otherwise unduly impair product performance, aesthetics or stability. The concentration of the optional additional surfactants in the personal care composition may vary with the cleansing or lather performance desired, the optional surfactant selected, the desired product concentration, the presence of other components in the composition, and other factors well known in the art.

Non limiting examples of other surfactants suitable for use in the personal care compositions are described in McCutcheon's, Emulsifiers and Detergents, 1989 Annual, published by M. C. Publishing Co., and U.S. Pat. Nos. 3,929,678; 2,658,072; 2,438,091; 2,528,378.

Aqueous Carrier

The personal care compositions include an aqueous carrier. The level and species of the carrier are selected according to the compatibility with other components and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Additional Cationic Polymers

In order to adjust rinse feel for specific consumer groups, one embodiment comprises blends of the synthetic copolymer with other traditional polymers such as cationic celluloses, cationic guars, cationic starches, or even other cationic synthetic polymers.

Cellulose or Guar Cationic Deposition Polymers

The personal care compositions may also comprise cellulose or guar cationic deposition polymers. Generally, such cellulose or guar cationic deposition polymers may be present at a concentration from about 0.05% to about 5%, by weight of the composition. Suitable cellulose or guar cationic deposition polymers have a molecular weight of greater than about 5,000. Additionally, such cellulose or guar deposition polymers have a charge density from about 0.5 meq/g to about 4.0 meq/g at the pH of intended use of the personal care composition, which pH will generally range from about pH 3 to about pH 9, preferably between about pH 4 and about pH 8. The pH of the compositions is measured neat.

Suitable cellulose or guar cationic polymers include those which conform to the following formula:

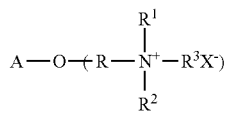

wherein A is an anhydroglucose residual group, such as a cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion. Non-limiting examples of such counterions include halides (e.g., chlorine, fluorine, bromine, iodine), sulfate and methylsulfate. The degree of cationic substitution in these polysaccharide polymers is typically from about 0.01 to about 1 cationic groups per anhydroglucose unit.

In one embodiment of the invention, the cellulose or guar cationic polymers are salts of hydroxyethyl cellulose reacted with trimethyl ammonium substituted epoxide, referred to in the industry (CTFA) as Polyquatemium 10 and available from Amerchol Corp. (Edison, N.J., USA).

Cationic Deposition Polymers

In addition to the synthetic cationic copolymers of the present invention, the personal care compositions herein may also comprise additional synthetic cationic deposition polymers. Generally, such synthetic cationic deposition polymers may be present at a concentration from about 0.025% to about 5%, by weight of the composition. Such synthetic cationic deposition polymers have a molecular weight from about 1,000 to about 5,000,000. Additionally, such synthetic cationic deposition polymers have a charge density from about 0.5 meq/g to about 10 meq/g.

Suitable synthetic cationic deposition polymers include those which are water-soluble or dispersible, cationic, non-crosslinked, conditioning copolymers comprising: (i) one or more cationic monomer units; and (ii) one or more nonionic monomer units or monomer units bearing a terminal negative charge; wherein said copolymer has a net positive charge, a cationic charge density of from about 0.5 meq/g to about 10 meg/g, and an average molecular weight from about 1,000 to about 5,000,000.

Non-limiting examples of suitable synthetic cationic deposition polymers are described in U.S. Patent Publication No. 2003/0223951 A1 to Geary et al.

Cationically Modified Starch Polymer

In addition to the synthetic cationic copolymers of the present invention, the personal care compositions herein may also comprise additional water-soluble cationically modified starch polymers. As used herein, the term "cationically modified starch" refers to a starch to which a cationic group is added prior to degradation of the starch to a smaller molecular weight, or to a starch to which a cationic group is added after modification of the starch to a desired molecular weight. The definition of the term "cationically modified starch" also includes amphoterically modified starch. The term "amphoterically modified starch" refers to a starch hydrolysate to which a cationic group and an anionic group are added.

In one embodiment, the personal care compositions comprise cationically modified starch polymers at a range of about 0.01% to about 10%, and more preferably from about 0.05% to about 5%, by weight of the composition.

The cationically modified starch polymers suitable for use in the personal care compositions have a molecular weight from about 1,000 to about 200,000. In one embodiment, the cationically modified starch polymers have a molecular weight from about 5,000 to about 100,000. The weight average molecular weight may be measured by gel permeation chromatography ("GPC") using an ALLIANCE® HPLC (Waters 2695 Separation Module) with two hydrogel columns in series (Waters Ultrahydrogel Linear 6-13 um, 7.8×300 nm GPC column, part number 011545) at a column temperature of 30° C. and at a flow rate of 0.9 ml/min, and using a VISCOTEK® Model 300 TDA (triple detector array), light scattering detector (single angle, 90°), viscosity detector, and refractive index detector, all at detector temperatures of 30° C., with a method created by using pullulan narrow standard P-800 from American Polymer Standards Corporation ($M_w$=788,000), with an injection volume of 25 to 100 μl, and using a do/dc of 0.147. Additional details on measuring the weight average molecular weight according to a GPC method are described in U.S. Patent Publication No. 2003/0154883 A1, entitled "Non-Thermoplastic Starch Fibers and Starch Composition for Making Same."

In one embodiment, the personal care compositions include cationically modified starch polymers which have a charge density from about 0.7 meq/g to about 7 meq/g. The chemical modification to obtain such a charge density includes, but is not limited to, the addition of amino and/or ammonium groups into the starch molecules.

Non-limiting examples of suitable cationically modified starch polymers are described in U.S. patent application Ser. No. 10/758,656 to Peffly et al.

Oily Conditioning Agent

In a preferred embodiment, the personal care compositions comprise one or more oily conditioning agents. Oily conditioning agents include materials which are used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The oily conditioning agents useful in the personal care compositions typically comprise a water-insoluble, water-dispersible, non-volatile, liquid that forms emulsified, liquid particles. Suitable oily conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

One or more oily conditioning agents are typically present at a concentration from about 0.01% to about 10%, preferably from about 0.1% to about 8%, more preferably from about 0.2% to about 4%, by weight of the composition.

In a preferred embodiment, the ratio of oily conditioning agent to synthetic cationic polymer is at least about 2:1

Silicone Conditioning Agent

The oily conditioning agents of the personal care compositions are preferably a water-insoluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the personal care compositions preferably have a viscosity, as measured at 25° C., from about 20 to about 2,000,000 centistokes ("csk"), more preferably from about 1,000 to about 1,800,000 csk, even more preferably from about 5,000 to about 1,500,000 csk, more preferably from about 10,000 to about 1,000,000 csk.

In one embodiment, the personal care composition is opaque. The personal care composition comprises a non-volatile silicone oil having a particle size as measured in the personal care composition from about 1 µm to about 50 µm. In an embodiment for small particle silicone application to the hair, the personal care composition comprises a non-volatile silicone oil having a particle size as measured in the personal care composition from about 100 nm to about 1 µm. A substantially clear composition embodiment comprises a non-volatile silicone oil having a particle size as measured in the personal care composition of less than about 100 nm.

The transparency of the composition is measured using Ultra-Violet/Visible (UV/IS) Spectrophotometry, which determines the absorption or transmission of UV/VIS light by a sample. A light wavelength of 600 nm is adequate for characterizing the degree of clarity of cosmetic compositions. Typically, it is best to follow the specific instructions relating the specific spectrophotometer being used. In general, the procedure for measuring percent transmittance starts by setting the spectrophotometer to the 600 nm. Then a calibration "blank" is run to calibrate the readout to 100 percent transmittance. The test sample is then placed in a cuvette designed to fit the specific spectrophotomer and the percent transmittance is measured by the spectrophotomer at 600 nm.

Non-volatile silicone oils suitable for use in compositions may be selected from organo-modified silicones and fluoro-modified silicones. In one embodiment, the non-volatile silicone oil is an organo-modified silicone which comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

In a preferred embodiment, the non-volatile silicone oil is dimethicone.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids suitable for use in the personal care compositions are disclosed in U.S. Pat. No. 2,826,551; U.S. Pat. No. 3,964,500; U.S. Pat. No. 4,364,837; British Patent No. 849,433, and *Silicon Compounds*, Petrarch Systems, Inc. (1984).

Organic Conditioning Oils

The oily conditioning agent of the personal care compositions may also comprise at least one organic conditioning oil, either alone or in combination with other conditioning agents, such as the silicones described above.

Hydrocarbon Oils

Suitable organic conditioning oils for use as conditioning agents in the personal care compositions comprise hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include 2,2,4,4,6,6,8,8-dimethyl-10-methylundecane and 2,2,4,4,6,6-dimethyl-8-methylnonane, available from Permethyl Corporation. A preferred hydrocarbon polymer is polybutene, such as the copolymer of isobutylene and butene, which is commercially available as L-14 polybutene from Amoco Chemical Corporation.

Polyolefins

Organic conditioning oils for use in the personal care compositions may also comprise liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

Fatty Esters

Other suitable organic conditioning oils for use as the conditioning agent in the personal care compositions include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the personal care compositions are those known as polyhydric alcohol esters. Such polyhydric alcohol esters include alkylene glycol esters.

Still other fatty esters suitable for use in the personal care compositions are glycerides, including, but not limited to, mono-, di-, and tri-glycerides, preferably di- and tri-glycerides, more preferably triglycerides. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones. Specific non-limiting examples of suitable fluorinated compounds include the FOMBLIN® product line from Ausimont which includes HC/04, HC/25, HC01, HC/02, HC/03; Dioctyldodecyl Fluoroeptyl Citrate, commonly called BIOSIL BASICS® Fluoro Gerbet 3.5 supplied by Biosil Technologies; and BIOSIL BASICS® Fluorosil LF also supplied by Biosil Technologies.

Fatty Alcohols

Other suitable organic conditioning oils for use in the personal care compositions comprise fatty alcohols having at least about 10 carbon atoms, more preferably about 10 to about 22 carbon atoms, most preferably about 12 to about 16 carbon atoms. Also suitable for use in the personal care compositions are alkoxylated fatty alcohols which conform to the general formula:

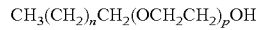

$$CH_3(CH_2)_nCH_2(OCH_2CH_2)_pOH$$

wherein n is a positive integer having a value from about 8 to about 20, preferably about 10 to about 14, and p is a positive integer having a value from about 1 to about 30, preferably from about 2 to about 23.

Alkyl Glucosides and Alkyl Glucoside Derivatives

Suitable organic conditioning oils for use in the personal care compositions comprise alkyl glucosides and alkyl glucoside derivatives. Specific non-limiting examples of suitable alkyl glucosides and alkyl glucoside derivatives include GLUCAM® E-10, GLUCAM® E-20, GLUCAM® P-10, and GLUCQUAT® 125 commercially available from Amerchol.

Other Conditioning Agents

Quaternary Ammonium Compounds

Suitable quaternary ammonium compounds for use as conditioning agents in the personal care compositions comprise hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

Examples of other useful quaternary ammonium surfactants include, but are not limited to, Quaternium-33, Quaternium-43, isostearamidopropyl ethyldimonium ethosulfate, Quaternium-22 and Quaternium-26, or combinations thereof, as designated in the CTFA Dictionary.

Other hydrophilic quaternary ammonium compounds useful in a composition of comprise Quaternium-16, Quaternium-27, Quaternium-30, Quaternium-52, Quaternium-53, Quaternium-56, Quaternium-60, Quaternium-61, Quaternium-62, Quaternium-63, Quaternium-71, and combinations thereof.

Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M, and mixtures thereof.

Additional Components

The personal care compositions may further comprise one or more additional components known for use in hair care or personal care products, provided that the additional components are physically and chemically compatible with the essential components described herein, or do not otherwise unduly impair product stability, aesthetics or performance. Individual concentrations of such additional components may range from about 0.001% to about 10% by weight of the personal care compositions.

Non-limiting examples of additional components for use in the composition include natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

Optional Components

Anti-Dandruff Actives

The personal care compositions may also comprise an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

Azole anti-microbials include imidazoles such as climbazole and ketoconazole.

Selenium sulfide compounds are described, for example, in U.S. Pat. No. 2,694,668; U.S. Pat. No. 3,152,046; U.S. Pat. No. 4,089,945; and U.S. Pat. No. 4,885,107.

Sulfur may also be used as a particulate anti-microbial/anti-dandruff agent in the personal care compositions.

The personal care compositions may further comprise one or more keratolytic agents such as salicylic acid.

Additional anti-microbial actives may include extracts of melaleuca (tea tree) and charcoal.

When present in the composition, the anti-dandruff active is included in an amount from about 0.01% to about 5%, preferably from about 0.1% to about 3%, and more preferably from about 0.3% to about 2%, by weight of the composition.

Particles

The personal care compositions may also comprise particles. Useful particles can be inorganic, synthetic, or semi-synthetic. In the present invention, it is preferable to incorporate no more than about 20%, more preferably no more than about 10% and even more preferably no more than 2%, by weight of the composition, of particles. In one embodiment, the particles have an average mean particle size of less than about 300 μm.

Non-limiting examples of inorganic particles include colloidal silicas, fumed silicas, precipitated silicas, silica gels, magnesium silicate, glass particles, talcs, micas, sericites, and various natural and synthetic clays including bentonites, hectorites, and montmorillonites.

Examples of synthetic particles comprise silicone resins, poly(meth)acrylates, polyethylene, polyester, polypropylene, polystyrene, polyurethane, polyamide (e.g., Nylon®), epoxy resins, urea resins, acrylic powders, and the like.

Non-limiting examples of hybrid particles include sericite & crosslinked polystyrene hybrid powder, and mica and silica hybrid powder.

Opacifying Agents

The personal care compositions may also comprise one or more opacifying agents. Opacifying agents are typically used in cleansing compositions to impart desired aesthetic benefits to the composition, such as color or pearlescence. In the present invention, it is preferable to incorporate from about 0.01% to about 20%, more preferably from about 0.01% to about 10% and even more preferably from about 0.01% to about 2%, by weight of the composition, of opacifying agents.

Suitable opacifying agents include, for example, fumed silica, polymethylmethacrylate, micronized Teflon®, boron nitride, barium sulfate, acrylate polymers, aluminum silicate, aluminum starch octenylsuccinate, calcium silicate, cellulose, chalk, corn starch, diatomaceous earth, Fuller's earth, glyceryl starch, hydrated silica, magnesium carbonate, magnesium hydroxide, magnesium oxide, magnesium trisilicate, maltodextrin, microcrystalline cellulose, rice starch, silica, titanium dioxide, zinc laurate, zinc myristate, zinc neodecanoate, zinc rosinate, zinc stearate, polyethylene, alumina, attapulgite, calcium carbonate, calcium silicate, dextran, nylon, silica silylate, silk powder, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The opacifying agents may also comprise various organic and inorganic pigments. The organic pigments are generally various aromatic types including azo, indigoid, triphenylmethane, anthraquinone, and xanthine dyes. Inorganic pigments include iron oxides, ultramarine and chromium or chromium hydroxide colors, and mixtures thereof.

Suspending Agents

The personal care compositions may further comprise a suspending agent at concentrations effective for suspending water-insoluble material in dispersed form in the compositions or for modifying the viscosity of the composition. Such concentrations generally range from about 0.1% to about 10%, preferably from about 0.3% to about 5.0%, by weight of the composition, of suspending agent.

Suspending agents useful herein include anionic polymers and nonionic polymers. Useful herein are vinyl polymers such as cross linked acrylic acid polymers with the CTFA name Carbomer.

Paraffinic Hydrocarbons

The personal care compositions may also comprise one or more paraffinic hydrocarbons. Paraffinic hydrocarbons suitable for use in compositions of the present invention include those materials which are known for use in hair care or other personal care compositions, such as those having a vapor pressure at 1 atm of equal to or greater than about 21° C. (about 70° F.). Non-limiting examples include pentane and isopentane.

Propellants

The personal care compositions may comprise one or more propellants. Propellants suitable for use in compositions of the present invention include those materials which are known for use in hair care or other personal care compositions, such as liquefied gas propellants and compressed gas propellants. Suitable propellants have a vapor pressure at 1 atm of less than about 21° C. (about 70° F.). Non-limiting examples of suitable propellants are alkanes, isoalkanes, haloalkanes, dimethyl ether, nitrogen, nitrous oxide, carbon dioxide, and mixtures thereof.

Mono or Divalent Salt

The personal care compositions may further comprise a mono or divalent salt, which acts as a source of entropy to assist in coacervate formation. Salt allows more contacts to be made between the polymer and surfactant, which increases the formation of coacervate. By the term "coacervate initiator," as used herein, means salt capable of inducing the formation of coacervates when combined with compositions comprising an anionic detersive surfactant component surfactant system and the synthetic cationic polymer.

Surfactant salts themselves are not included in the present salt definition but other salts are. Suitable salts comprise chlorides, phosphates, sulfates, nitrates, citrates and halides. The counter ions of such salts can be, but are not limited to, sodium, potassium, ammonium, magnesium, zinc or other mono and divalent cation. Salts most preferred for use in the compositions of the present invention include sodium chloride, ammonium chloride, sodium citrate, magnesium chloride, and magnesium sulfate. It is recognized that these salts may serve as thickening aids or buffering aids in addition to their role as a coacervate initiator. The amount of coacervate initiator comprising the salt and/or the optional surfactant will vary with the type of surfactant and polymer, but is preferably present at a level of from about 0.01% to about 5%, more preferably from about 0.05% to about 3.5%, and still more preferably from about 0.1% to about 2%.

Other Optional Components

The personal care compositions may contain fragrance.

The personal care compositions may also comprise water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts.

The compositions of the present invention may also contain chelating agents.

The compositions of present invention may further comprise materials useful for hair loss prevention and hair growth stimulants or agents.

Method for Measuring Lather Volume

The potential for the personal care compositions disclosed herein to generate lather is measured via the SITA Foam Tester (model: R-2000) made by SITA Messtechnik GmbH (Germany). The SITA Foam Tester R-2000 utilizes a patented rotor of defined geometry for foam generation. The rotor mechanically inserts air bubbles into the liquid. The foam volume is measured by an array of sensor needles, which scans the foam surface. Using an array of sensor needles permits exact measurement of the foam volume even with uneven foam surfaces. The output is given as average millimeters of foam height per measure. Foam height measurements are taken every 10 seconds. The stir count and stir time refer to the input in the SITA program. The SITA program stirs for 10 sec then a measure is taken, then stirs again for 10 seconds a measure is taken—this occurs 12 times in total (stirred for 12 separate 10 sec. intervals). The Stir Count, as used herein, means the total number of stirring intervals in one test. It has been found that the 40 second measurement, the fourth total measurement, is particularly relevant to the consumer usage experience. At the 40 second measurement, foam heights of at least about 50 millimeters are particularly desirable, even more preferred are foam heights of at least about 100 millimeters. To measure these values, standard manufacturer's methods are followed for operation of the equipment with the following requirements:

Instrument Settings/Measurement Parameters:

| | |
|---|---|
| Volume of Water (ml) | 300 |
| Mixing Rotor Speed (rpm) | 1000 |
| Stir Count | 12 |
| Stir Time (sec) | 10 |

Water/Product/Soil Load:

| |
|---|
| 300 gm of 7 grain hardness water at 100° F. |
| 0.5 ml test product (cleansing composition) |
| 0.05 ml Extra Virgin, first cold pressed Olive Oil (simulates sebum) |

The above materials may either be premixed prior to being fed into the SITA unit or the water may be metered in and the test product and soil may be injected into the SITA vessel either at the top of the vessel or through the injection port.

Method of Making

The personal care compositions may be made by mixing the ingredients together at either room temperature or at elevated temperature, e.g., about 72° C. Heat only needs to be used if solid ingredients are to be incorporated into the composition. The ingredients are mixed at the batch processing temperature. Additional ingredients, including electrolytes, polymers, fragrance, and particles, may be added to the product at room temperature.

Method of Treating Hair or Skin

The personal care compositions are used in a conventional manner for cleansing and conditioning hair or skin. Generally, a method of treating hair or skin of the present invention comprises applying the personal care composition of the present invention to the hair or skin. More specifically, an effective amount of the personal care composition is applied to the hair or skin, which has preferably been wetted with water, and then the personal care composition is rinsed off. Such effective amounts generally range from about 1 g to about 50 g, preferably from about 1 g to about 20 g. Application to the hair typically includes working the composition through the hair such that most or all of the hair is contacted with the composition.

This method for treating the hair or skin comprises the steps of: (a) applying an effective amount of the personal care composition to the hair or skin, and (b) rinsing the applied areas of hair or skin with water. These steps can be repeated as many times as desired to achieve the desired cleansing and conditioning benefit.

For use in methods of the present invention, the personal care composition may be in various forms, for example, shampoos, body washes, gels, lotions, creams, mousses, and sprays. For some of these forms, the personal care composition may be packaged in a pump-dispenser bottle or in an aerosol container. In other useful forms, the personal care composition may be dried to a film or a powder, or it may be applied to a substrate which is then used for application to the hair or skin.

NON-LIMITING EXAMPLES

The compositions illustrated in the following Examples illustrate specific embodiments of the compositions of the present invention, but are not intended to be limiting thereof. Other modifications can be undertaken by the skilled artisan without departing from the spirit and scope of this invention. These exemplified embodiments of the composition of the present invention provide enhanced deposition of conditioning agents to the hair and/or skin.

The compositions illustrated in the following Examples are prepared by conventional formulation and mixing methods, an example of which is described above. All exemplified amounts are listed as weight percents and exclude minor materials such as diluents, preservatives, color solutions, imagery ingredients, botanicals, and so forth, unless otherwise specified.

The following are representative of personal care compositions of the present invention:

| | EXAMPLE COMPOSITION | | | | | | |
|---|---|---|---|---|---|---|---|
| | I | II | III | IV | V | VI | VII |
| Ingredient | | | | | | | |
| Water | q.s. | q.s. | q.s. | q.s. | q.s. | q.s. | q.s. |
| AM:TRIQUAT Copolymer [1] | 0.25 | — | 0.25 | — | 0.25 | — | 0.25 |
| AM:TRIQUAT Copolymer [2] | — | 0.25 | — | 0.25 | — | 0.25 | — |
| Sodium Laureth Sulfate (SLE3S) [3] | — | 6.00 | 8.00 | 8.00 | 10.00 | 12.00 | 14.00 |
| Sodium Lauryl Sulfate (SLS) [4] | — | 10.00 | — | 6.00 | — | — | — |
| Ammonium Laureth Sulfate (ALE3S) [5] | 6.00 | — | — | — | — | — | — |
| Ammonium Lauryl Sulfate (ALS) [6] | 10.00 | — | — | — | — | — | — |
| Cocoamidopropyl Betaine [7] | — | — | 4.00 | 2.00 | 2.00 | 4.00 | 4.00 |
| PPG-2 Hydroxyethyl Coco/Isostearamide [8] | — | 2.00 | 2.00 | 2.00 | 2.00 | 2.00 | 2.00 |
| Sodium Chloride [9] | 2.50 | 2.25 | 1.50 | 0.50 | 1.00 | — | 1.50 |
| Sodium Xylene Sulfonate [10] | — | — | — | — | — | 0.25 | — |
| Fragrance | 0.70 | 0.70 | 0.70 | 0.70 | 0.70 | 0.70 | 0.70 |
| Preservatives, pH adjusters | Up to 1% | Up to 1% | Up to 1% | Up to 1% | Up to 1% | Up to 1% | Up to 1% |
| Calculated: | | | | | | | |
| Ethoxylate Level | 1.77 | 1.77 | 2.35 | 2.35 | 2.94 | 3.53 | 4.12 |
| Sulfate Level | 3.80 | 3.80 | 1.51 | 3.11 | 1.88 | 2.26 | 2.64 |
| Ethoxylate:Sulfate (Ratio) | 0.46 | 0.46 | 1.56 | 0.76 | 1.56 | 1.56 | 1.56 |

[1] Copolymer of Acrylamide(AM) and TRIQUAT, MW = 1,000,000; CD = 1.6 meq./gram; AM:TRIQUAT ratio = 5
[2] Copolymer of Acrylamide(AM) and TRIQUAT, MW = 400,000; CD = 1.6 meq./gram; AM:TRIQUAT ratio = 50
[3] Sodium Laureth Sulfate, supplier: P&G
[4] Sodium Lauryl Sulfate, supplier: P&G
Ammonium Laureth Sulfate, supplier: P&G
Ammonium Lauryl Sulfate, supplier: P&G
[5] Tegobetaine F-B, supplier: Goldschmidt Chemicals
[6] Promidium 2, supplier Unichema
[7] Sodium Chloride USP (food grade), supplier Morton
[8] Sodium Xylene Sulfonate, supplier: Stepan

| | EXAMPLE COMPOSITION | | | | | | |
|---|---|---|---|---|---|---|---|
| | VIII | IX | X | XI | XII | XIII | XIV |
| Ingredient | | | | | | | |
| Water | q.s. | q.s. | q.s. | q.s. | q.s. | q.s. | q.s. |
| AM:TRIQUAT Copolymer [1] | 0.25 | — | 0.25 | — | 0.25 | — | 0.25 |
| AM:TRIQUAT Copolymer [2] | — | 0.25 | — | 0.25 | — | 0.25 | — |
| Sodium Laureth Sulfate (SLE3S) [3] | 6.00 | 6.00 | 8.00 | 8.00 | 10.00 | 12.00 | 14.00 |
| Sodium Lauryl Sulfate (SLS) [4] | 10.00 | 10.00 | — | 6.00 | — | — | — |
| Dimethiconol Microemulsion A [5] | — | — | — | 1.00 | — | — | — |
| Dimethiconol Microemulsion B [6] | 1.00 | 1.00 | 1.00 | — | — | — | — |
| Disodium Coco Amphodiacetate [7] | — | — | 2.00 | 2.00 | 2.00 | 4.00 | 4.00 |
| Cocoamidopropyl Betaine [8] | — | 2.00 | — | 2.00 | 2.00 | 2.00 | 2.00 |
| PPG-2 Hydroxyethyl Coco/Isostearamide [9] | — | 2.00 | — | 2.00 | 2.00 | 2.00 | 2.00 |
| Cocoamide MEA [10] | 1.50 | — | 0.80 | — | — | — | — |
| Sodium Chloride [11] | 0.25 | 2.00 | 3.00 | 1.50 | 1.50 | 1.00 | 1.50 |
| Fragrance | 0.70 | 0.70 | 0.70 | 0.70 | 0.70 | 0.70 | 0.70 |
| Preservatives, pH adjusters | Up to 1% | Up to 1% | Up to 1% | Up to 1% | Up to 1% | Up to 1% | Up to 1% |
| Calculated: | | | | | | | |
| Ethoxylate Level | 1.77 | 1.77 | 2.35 | 2.35 | 2.94 | 3.53 | 4.12 |
| Sulfate Level | 3.80 | 3.80 | 1.51 | 3.11 | 1.88 | 2.26 | 2.64 |
| Ethoxylate:Sulfate (Ratio) | 0.46 | 0.46 | 1.56 | 0.76 | 1.56 | 1.56 | 1.56 |

[1] Copolymer of Acrylamide(AM) and TRIQUAT, MW = 1,000,000; CD = 1.6 meq./gram; AM:TRIQUAT ratio = 5
[2] Copolymer of Acrylamide(AM) and TRIQUAT, MW = 400,000; CD = 1.6 meq./gram; AM:TRIQUAT ratio = 50
[3] Sodium Laureth Sulfate, supplier: P&G
[4] Sodium Lauryl Sulfate, supplier: P&G
[5] Dow Corning Silicone Micro-emulsion DC2-1870; Internal Phase Viscosity = 72,000; 30 nm particle size dimethiconol using TEA dodecyl benzene sulfonate and laureth 23 as primary surfactants
[6] Dow Corning DC 2-1865; Internal Phase Viscosity = 25,000 cps; 25 nm particle size dimethiconol using TEA dodecyl benzene sulfonate and laureth 23 as primary surfactants
[7] Miranol C2M Conc NP, supplier: Rhodia.
[8] Tegobetaine F-B, supplier: Goldschmidt Chemicals
[9] Promidium 2, supplier Unichema
[10] Monamid CMA, supplier Goldschmidt Chemical
[11] Sodium Chloride USP (food grade), supplier Morton.

|  | EXAMPLE COMPOSITION | | | | |
| --- | --- | --- | --- | --- | --- |
|  | XV | XVI | XVII | XVIII | XIX |
| Ingredient | | | | | |
| Water | q.s. | q.s. | q.s. | q.s. | q.s. |
| AM:TRIQUAT Copolymer [1] | 0.25 | 0.25 | 0.25 | — | 0.25 |
| AM:TRIQUAT Copolymer [2] | — | — | — | 0.25 | — |
| Sodium Laureth Sulfate (SLE3S) [3] | — | 10.00 | — | 8.00 | 14.00 |
| Sodium Lauryl Sulfate (SLS) [4] | — | — | — | 3.00 | — |
| Ammonium Laureth Sulfate (ALE3S) [5] | 6.00 | — | 14.00 | — | — |
| Ammonium Lauryl Sulfate (ALS) [6] | 10.00 | — | 2.00 | — | — |
| Dimethicone Emulsion [5] | 1.00 | 2.00 | 1.00 | 0.50 | 1.00 |
| Disodium Coco Amphodiacetate [6] | — | 2.00 | — | — | — |
| Cocoamidopropyl Betaine [7] | — | — | 2.00 | 4.00 | 2.00 |
| PPG-2 Hydroxyethyl Coco/Isostearamide [8] | 2.00 | 2.00 | 2.00 | — | 2.00 |
| Ethylene Glycol Distearate [9] | 1.50 | — | — | — | 1.50 |
| Sodium Chloride [10] | 1.25 | 1.25 | 1.25 | 1.00 | 1.50 |
| Fragrance | 0.70 | 0.70 | 0.70 | 0.70 | 0.70 |
| Preservatives, pH adjusters | Up to 1% | Up to 1% | Up to 1% | Up to 1% | Up to 1% |
| Calculated: | | | | | |
| Ethoxylate Level | 1.77 | 2.94 | 4.12 | 2.35 | 4.12 |
| Sulfate Level | 3.80 | 1.88 | 3.17 | 2.31 | 2.64 |
| Ethoxylate:Sulfate (Ratio) | 0.46 | 1.56 | 1.30 | 1.02 | 1.56 |

[1] Copolymer of Acrylamide(AM) and TRIQUAT, MW = 1,000,000; CD = 1.6 meq./gram; AM:TRIQUAT ratio = 5
[2] Copolymer of Acrylamide(AM) and TRIQUAT, MW = 400,000; CD = 1.6 meq./gram; AM:TRIQUAT ratio = 50
[3] Sodium Laureth Sulfate, supplier: P&G
[4] Sodium Lauryl Sulfate, supplier: P&G
[5] Dow Corning Dimethicone emulsion DC-1664; 3 micron particle size
[6] Miranol C2M Conc NP, supplier: Rhodia.
[7] Tegobetaine F-B, supplier: Goldschmidt Chemicals
[8] Promidium 2, supplier Unichema
[9] Ethylene Glycol Distearate, EGDS Pure, supplier Goldschmidt Chemical
[10] Sodium Chloride USP (food grade), supplier Morton.

|  | EXAMPLE COMPOSITION | | | | |
| --- | --- | --- | --- | --- | --- |
|  | XX | XXI | XXII | XXIII | XXIV |
| Ingredient | | | | | |
| Water | q.s. | q.s. | q.s. | q.s. | q.s. |
| AM:TRIQUAT Copolymer [1] | 0.25 | 0.25 | 0.25 | — | 0.25 |
| AM:TRIQUAT Copolymer [2] | — | — | — | 0.25 | — |
| Sodium Laureth Sulfate (SLE3S) [3] | — | 6.00 | 8.00 | 8.00 | — |
| Sodium Lauryl Sulfate (SLS) [4] | — | 10.00 | 8.00 | 10.00 | — |
| Ammonium Laureth Sulfate (ALE3S) [5] | 6.00 | — | — | — | 15.00 |
| Ammonium Lauryl Sulfate (ALS) [6] | 10.00 | — | — | — | 2.00 |
| Dimethicone [5] | 1.20 | 0.5 | 1.00 | 0.50 | 1.00 |
| Cocoamidopropyl Betaine [6] | — | — | 2.00 | 1.00 | 5.00 |
| Cocoamide MEA [7] | 1.5 | 0.75 | — | — | — |
| Ethylene Glycol Distearate [8] | 1.50 | 1.50 | 1.50 | 1.50 | 1.50 |
| Sodium Chloride [9] | 1.50 | 1.25 | 1.00 | 1.25 | 1.50 |
| Fragrance | 0.70 | 0.70 | 0.70 | 0.70 | 0.70 |
| Preservatives, pH adjusters | Up to 1% | Up to 1% | Up to 1% | Up to 1% | Up to 1% |
| Calculated: | | | | | |
| Ethoxylate Level | 1.77 | 1.77 | 2.35 | 2.35 | 4.41 |
| Sulfate Level | 3.80 | 3.80 | 3.64 | 4.17 | 3.36 |
| Ethoxylate:Sulfate (Ratio) | 0.46 | 0.46 | 0.65 | 0.56 | 1.31 |

[1] Copolymer of Acrylamide(AM) and TRIQUAT, MW = 1,000,000; CD = 1.6 meq./gram; AM:TRIQUAT ratio = 5
[2] Copolymer of Acrylamide(AM) and TRIQUAT, MW = 400,000; CD = 1.6 meq./gram; AM:TRIQUAT ratio = 50
[3] Sodium Laureth Sulfate, supplier: P&G
[4] Sodium Lauryl Sulfate, supplier: P&G
[5] Dimethicone Fluid, Viscasil 330M; 30 micron particle size; supplier: General Electric Silicones
[6] Tegobetaine F-B, supplier: Goldschmidt Chemicals
[7] Monamid CMA, supplier Goldschmidt Chemical
[8] Ethylene Glycol Distearate, EGDS Pure, supplier Goldschmidt Chemical
[9] Sodium Chloride USP (food grade), supplier Morton.

|  | EXAMPLE COMPOSITION | | | | |
| --- | --- | --- | --- | --- | --- |
|  | XXV | XXVI | XXVII | XXVIII | XXIX |
| Ingredient |  |  |  |  |  |
| Water | q.s. | q.s. | q.s. | q.s. | q.s. |
| AM:TRIQUAT Copolymer [1] | 0.25 | 0.25 | — | 0.25 | 0.10 |
| AM:TRIQUAT Copolymer [2] | — | — | 0.25 | — | — |
| Polyquaternium 10 [3] | 0.10 | — | — | — | 0.10 |
| Polyquaternium 10 [4] | — | 0.10 | — | — | — |
| Polyquaternium 10 [5] | — | — | 0.10 | — | — |
| Guar Hydroxypropyl Trimonium Chloride [6] | — | — | — | 0.10 | — |
| Sodium Laureth Sulfate (SLE3S) [7] | 10.00 | 8.00 | 6.00 | 10.00 | 8.00 |
| Sodium Lauryl Sulfate (SLS) [8] | 4.00 | 6.00 | 10.00 | 6.00 | 10.00 |
| Dimethiconol Microemulsion A [9] | 1.00 | — | — | — | 0.50 |
| Dimethiconol Microemulsion B [10] | — | 1.00 | 1.00 | 1.00 | — |
| Cocoamdopropyl Betaine [13] | 2.00 | 4.00 | 4.00 | 2.00 | — |
| PPG-2 Hydroxyethyl Coco/Isostearamide [14] | 2.00 | — | — | 1.00 | 2.00 |
| Sodium Chloride [15] | 1.25 | 1.00 | 1.25 | 1.25 | 1.00 |
| Fragrance | 0.70 | 0.70 | 0.70 | 0.70 | 0.70 |
| Preservatives, pH adjusters | Up to 1% | Up to 1% | Up to 1% | Up to 1% | Up to 1% |
| Calculated: |  |  |  |  |  |
| Ethoxylate level | 2.94 | 2.35 | 1.77 | 2.94 | 2.35 |
| Sulfate level | 2.95 | 3.11 | 3.80 | 3.48 | 4.17 |
| Ethoxylate:Sulfate (Ratio) | 1.00 | 0.76 | 0.46 | 0.84 | 0.56 |

[1] Copolymer of Acrylamide(AM) and TRIQUAT, MW = 1,000,000; CD = 1.6 meq./gram; AM:TRIQUAT ratio = 5
[2] Copolymer of Acrylamide(AM) and TRIQUAT, MW = 400,000; CD = 1.6 meq./gram; AM:TRIQUAT ratio = 50
[3] Polyquaterium 10 polymer with MW = 2.0 MM and charge density = 0.7
[4] UCare Polymer JR30M, MW = 2.0 MM, charge density = 1.32 meq./gram, supplier Dow Chemicals
[5] UCare Polymer KG30M, MW = 2.0 MM, charge density = 1.96 meq./gram, supplier Dow Chemicals
[6] Jaguar Excel, supplier: Rhodia.
[7] Sodium Laureth Sulfate, supplier: P&G
[8] Sodium Lauryl Sulfate, supplier: P&G
[9] Dow Corning Silicone Micro-emulsion DC2-1870; Internal Phase Viscosity = 72,000; 30 nm particle size dimethiconol using TEA dodecyl benzene sulfonate and laureth 23 as primary surfactants
[10] Dow Corning DC2-1865 batch#19238-8; Internal Phase Viscosity = 25,000 cps; 25 nm particle size dimethiconol using TEA dodecyl benzene sulfonate and laureth 23 as primary surfactants
[11] Tegobetaine F-B, supplier: Goldschmidt Chemicals
[12] Promidium 2, supplier Unichema
[13] Sodium Chloride USP (food grade), supplier Morton.

|  | EXAMPLE COMPOSITION | | | | | |
| --- | --- | --- | --- | --- | --- | --- |
|  | XXXVII | XXXVIII | XXXIX | XL | XLI | XLII |
| Ingredient |  |  |  |  |  |  |
| Water | q.s. | q.s. | q.s. | q.s. | q.s. | q.s. |
| AM:TRIQUAT Copolymer [1] | 0.25 | 0.50 | — | 0.50 | 0.1 | 0.25 |
| Sodium Laureth Sulfate [2] | 6.00 | 8.00 | 10.00 | 8.00 | 8.00 | 12.00 |
| Sodium Lauryl [3] | 10.00 | 8.00 | 6.00 | — | — | 2.00 |
| Aminosilicone [4] | 2.00 | — | — | — | — | — |
| Aminosilicone [5] | — | — | — | — | — | 2.00 |
| Di-PPG-2 Myreth-10 Adipate [6] | — | 1.00 | — | — | — | — |
| Zinc Pyrithione [7] | — | — | — | — | — | 1.00 |
| Cocoamdopropyl Betaine [8] | — | 2.00 | 2.00 | 8.00 | 8.00 | 2.00 |
| Silica [9] | — | 1.00 | — | — | — | — |
| Silica [10] | — | — | 1.00 | — | — | — |
| Silica [11] | — | — | — | 1.00 | — | — |
| Silica [12] | — | — | — | — | 1.00 | — |
| Polymethylsilsesquioxane A [13] | — | — | 1.00 | — | — | — |
| Polymethylsilsesquioxane B [14] | — | — | — | 1.00 | — | — |
| PPG-2 Hydroxyethyl Coco/Isostearamide [15] | 2.00 | 2.00 | — | 2.00 | 2.00 | 2.00 |
| Ethylene Glycol Distearate [16] | 1.50 | 1.50 | 1.50 | 1.50 | 1.50 | 1.50 |
| Sodium Chloride [17] | 1.50 | 1.50 | 1.50 | 1.50 | 1.50 | 1.50 |
| Fragrance | 0.70 | 0.70 | 0.70 | 0.70 | 0.70 | 0.70 |
| Preservatives, pH adjusters | Up to 1% | Up to 1% | Up to 1% | Up to 1% | Up to 1% | Up to 1% |
| Calculated: |  |  |  |  |  |  |
| Ethoxylate level | 1.77 | 2.35 | 2.94 | 2.35 | 2.35 | 3.53 |
| Sulfate level | 3.80 | 3.64 | 3.48 | 1.51 | 1.51 | 2.79 |
| Ethoxylate:Sulfate (Ratio) | 0.46 | 0.65 | 0.84 | 1.56 | 1.56 | 1.26 |

[1] Copolymer of Acrylamide(AM) and TRIQUAT, MW = 400,000; CD = 1.6 meq./gram; AM:TRIQUAT ratio = 50
[2] Sodium Laureth Sulfate, supplier: P&G
[3] Sodium Lauryl Sulfate, supplier: P&G

[4] Aminosilicone; supplier General Electric; terminal aminopropyl substitution, viscosity 350,000, D 1600, M' = 2, particle size 3 μm
[5] DC 2-8194 Aminosilicone; supplier Dow Corning, particle size ~30 nm
[6] Cromollient SCE, supplier Croda
[7] Zinc Pyrithione, supplier: Arch Chemicals
[8] Tegobetaine F-B, supplier: Goldschmidt Chemical
[9] Sipernat 22LS, supplier: Degussa
[10] MSS-500/H, supplier: General Electric Silicones
[11] MSS-500/N, supplier: General Electric Silicones
[12] Syloid 244FP Silica, supplier: Grace Davison
[13] Tospearl 240, supplier: General Electric Silicones
[14] Tospearl 3120, supplier: General Electric Silicones
[15] Promidium 2, supplier Unichema
[16] Ethylene Glycol Distearate, EGDS Pure, supplier Goldschmidt Chemical
[17] Sodium Chloride USP (food grade), supplier Morton The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein are, in relevant part, incorporated herein by reference: the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A personal care composition comprising:
    a) a synthetic random copolymer having a net positive charge comprising;
        i) a nonionic monomer unit of the following formula:

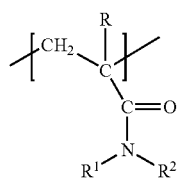

where R is H or $C_{1-4}$ alkyl; and $R^1$ and $R^2$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and
        ii) a cationic monomer unit with 2 or more positive charges of the following formula:

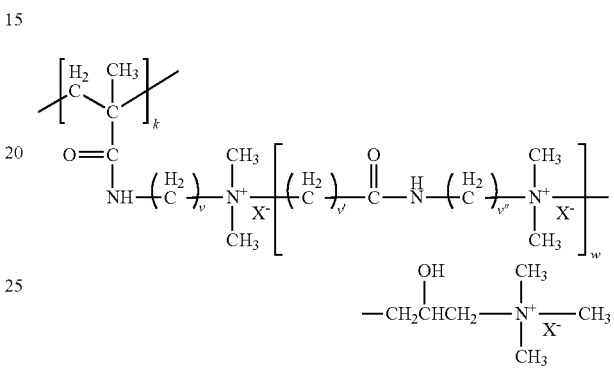

where k=1, each of v, v', and v" is independently an integer of from 1 to 6, w is zero or an integer of from 1 to 10, and $X^-$ is an anion; and
        iii) wherein the synthetic random copolymer comprises from about 0.5 to about 50%, by weight, of the cationic monomer;
    b) a detersive surfactant wherein said detersive surfactant comprises at least one anionic surfactant having an ethoxylate level and an anion level;
    wherein said ethoxylate level is from about 1 to about 10, and wherein said anion level is from about 1 to about 10; and
    c) an aqueous carrier.

2. A personal care composition according to claim 1 wherein R, $R^1$ and $R^2$ of said nonionic monomer unit are H and further wherein v=3 and w=1 in said cationic monomer unit.

3. A personal care composition according to claim 1 wherein said synthetic random copolymer is present in an amount from about 0.075% to about 1%, by weight of said personal care composition.

4. A personal care composition according to claim 1, wherein said detersive surfactant is selected from the group consisting of sulfates, sulfonates, sulfosuccinates, isethionates, carboxylates, phosphates, phosphonates and mixtures thereof.

5. A personal care composition according to claim 1, wherein said detersive surfactant is selected from the group consisting of amphoteric surfactants, zwitterionic surfactants, cationic surfactants, nonionic surfactants and mixtures thereof.

6. A personal care composition according to claim 5 wherein said amphoteric or zwitterionic surfactant is selected from the group consisting of cocoamidopropyl betaine, coco betaine, cocoamphoacetate, cocoamphodiacetate, lauroamphoacetate, lauroamphodiacetate, lauramine oxide and mixtures thereof.

7. A personal care composition according to claim 1 wherein lather volume is from about 50 ml to about 500 ml at the 40 second measurement.

8. A personal care composition according to claim 1 wherein said synthetic random copolymer is present in an amount from about 0.01% to about 5% by weight of said personal care composition.

9. A personal care composition according to claim 1 wherein said synthetic random copolymer has a linear charge density from at least about 2 meq/A to about 500 meq/A.

10. A personal care composition according to claim 1 wherein said synthetic random copolymer has a mass charge density from about 0.1 meq/gm to about 6.0 meq/gm.

11. A personal care composition according to claim 1 wherein said synthetic random copolymer has a molecular weight from about 10,000 to about 10,000,000.

12. A personal care composition according to claim 1, further comprising a cationic guar, cationic cellulose polymer, or a cationic modified starch polymer.

13. A personal care composition according to claim 1, further comprising at least one conditioning agent.

14. A personal care composition according to claim 13, wherein said conditioning agent is present in an amount from about 0.01 wt. % to about 10 wt. %.

15. A personal care composition according to claim 13, wherein said conditioning agent is selected from the group consisting of silicone conditioning agents, hydrocarbon oils, polyolefins, fatty alcohols, fatty esters, and mixtures thereof.

16. A personal care composition according to claim 15, wherein said silicone conditioning agent has a particle size of less than or equal to about 50 μm.

17. A personal care composition according to claim 15, wherein said silicone conditioning agent is selected from the group consisting of organo-modified silicones and fluoro-modified silicones.

18. A personal care composition according to claim 17, wherein said organo-modified silicone comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

19. A personal care composition according to claim 1, further comprising one or more additional components selected from the group consisting of anti-dandruff actives, particles, opacifying agents, suspending agents, paraffinic hydrocarbons, propellants, and a mono- or divalent salt.

20. A personal care composition comprising:
a) a synthetic random copolymer having a net positive charge comprising:
i) a nonionic monomer unit of the following formula:

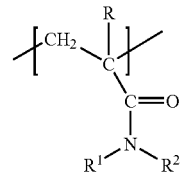

where R is H or $C_{1-4}$ alkyl; and $R^1$ and $R^2$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and ii) a cationic monomer unit with 2 or more positive charges of the following formula:

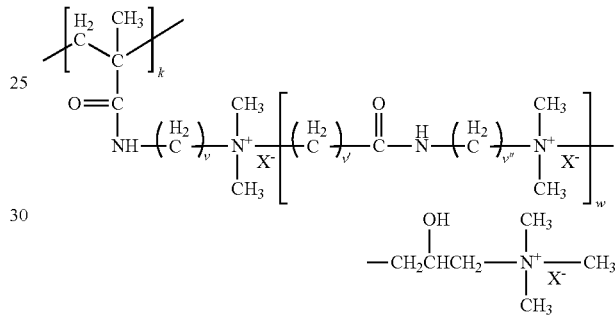

where k=1, each of v, v', and v" is independently an integer of from 1 to 6, w is zero or an integer of from 1 to 10, and $X^-$ is an anion; and iii) wherein the synthetic random copolymer comprises from about 1 to about 30%, by weight, of the cationic monomer;

b) a detersive surfactant wherein said detersive surfactant comprises at least one anionic surfactant having an ethoxylate level and an anion level;

wherein said ethoxylate level is from about 1 to about 10, and wherein said anion level is from about 1 to about 10; and c) an aqueous carrier.

* * * * *